(12) United States Patent
Karube et al.

(10) Patent No.: US 6,753,171 B2
(45) Date of Patent: Jun. 22, 2004

(54) SITE-SPECIFIC CELL PERFORATION TECHNIQUE

(75) Inventors: Isao Karube, Kanagawa (JP); Takashi Saitoh, Tokyo (JP)

(73) Assignee: Center for Advanced Science and Technology Incubation, Ltd., Tokyo (JP)

( * ) Notice: Subject to any disclaimer, the term of this patent is extended or adjusted under 35 U.S.C. 154(b) by 0 days.

(21) Appl. No.: 09/623,970

(22) PCT Filed: Mar. 12, 1999

(86) PCT No.: PCT/JP99/01223
§ 371 (c)(1),
(2), (4) Date: Dec. 28, 2000

(87) PCT Pub. No.: WO99/46361
PCT Pub. Date: Sep. 16, 1999

(65) Prior Publication Data
US 2003/0180946 A1 Sep. 25, 2003

(30) Foreign Application Priority Data
Mar. 12, 1998 (JP) .......................................... 10-080177

(51) Int. Cl.⁷ ........................ C12N 15/09; C12N 15/85; C12N 15/86; C12N 15/87; C12N 15/63
(52) U.S. Cl. ................ 435/173.5; 435/173.1; 435/325; 435/449; 435/455; 435/460
(58) Field of Search ............................. 435/173.5, 449, 435/455, 460, 173.1, 325

(56) References Cited

FOREIGN PATENT DOCUMENTS

GB 2209468 * 5/1989

OTHER PUBLICATIONS

Sambrook et al. Molecular Cloning A Laboratory Manual Second Edition Cold Spring Harbor Laboratory Press 1989 16.30–16.31 and 16.48–16.53.*

Saito et al. Light dose and time dependency of photodynamic cell membrane damage Photochemistry, 1998 68(5) 745–748.*
Hamill et al., "Improved Patch–Clamp Techniques for High– Resolution Current Recording from Cells and Cell––Free Membrane Patches," *Pflügers Arch.* 391:85–100 (1981).
Kurata et al., "The Laser Method for Efficient Introduction of Foreign DNA into Cultured Cells," *Experimental Cell Research* 162:372–378 (1986).
Valenzeno, "Photomodification of Biological Membranes with Emphasis on Singlet Oxygen Mechanisms," *Photochemistry and Photobiology* 46(1):147–160 (1987).
Horn et al., "Muscarnic Activation of Ionic Currents Measured by a New Whole–Cell Recording Method," *J. Gen. Physiol.* 92:145–159 (1988).
Levitan et al., "Neuropeptide Modulation of Single Calcium and Potassium Channels Detected with a New Patch Clamp Configuration," *Nature* 348:545–547 (1990).

(List continued on next page.)

*Primary Examiner*—Gerry Leffers
*Assistant Examiner*—Ramin Akhavan
(74) *Attorney, Agent, or Firm*—Nixon Peabody LLP

(57) ABSTRACT

A technique for controlling membrane denaturation reactions other than physical shear force was developed. For example, the present invention provides, a method for causing membrane disruption at a specific site by reacting a stimulus such as light with a compound that is activated by the stimulus, where the reaction occurs on a membrane such as a biomembrane. It also provides a membrane structure such as cells in which a specific site has been disrupted, which are obtained by the present method. Introduction of substances such as genes also became possible by using this membrane structure. Further provided is a membrane-destroying member for disrupting a membrane at a specific site. Thus, the present invention enabled, for example, easy membrane penetration using components constituting microelectrodes, micromanipulators, and microinjectors, which were conventionally hardly usable in penetrating cell membranes.

2 Claims, 13 Drawing Sheets

OTHER PUBLICATIONS

Marles et al., "Thiophenes as Mosquito Larvicides: Structure–Toxicity Relationship Analysis," *Pesticide Biochemistry and Physiology* 41:89–100 (1991).

Altin et al., "Testing the In Vivo Role of Protein Kinase C and c–Fos in Neurite Outgrowth by Microinjection of Antibodies into PC12 Cells," *Molecular Biology of the Cell* 3:323–333 (1992).

Thorpe et al., "Dynamics of Photoinduced Cell Plasma Membrane Injury," *Biophysical Journal* 68:2198–2206 (1995).

Haydon et al., "Membrane Deformation of Living Glial Cells Using Atomic Force Microscopy," *Journal of Microscopy* 182:114–120 (1996).

Boch et al., "Study of Photoinduced Energy and Electron Transfer in α–Terthienyl–Bovine Serum Albumin Conjugates: A Laser Flash Photolysis Study," *Photochemistry and Photobiology* 64(1):92–99 (1996).

Henriksen et al., "Laser–Assisted Patch Clamping: A Methodology," *Pflügers Arch.—Eur. J. Physiol.* 433:832–841 (1997).

* cited by examiner

1 Membrane structure
2 Support
3 Membrane denaturation promoting portion
4 Denatured portion of membrane 1 Membrane structure
2 Support
3 Membrane denaturation promoting portion
4 Denatured portion of membrane 1 Membrane structure
2 Support
3 Membrane denaturation promoting portion
4 Denatured portion of membrane 1 Membrane structure
2 Support
3 Liquid containing membrane denaturation promoter
4 Denatured portion of membrane 1 Membrane structure
2 Support
3 Membrane denaturation promoting portion
4 Denatured portion of membrane 1) Execute normal microinjection to check whether Z limit has been appropriately set 2) Change settings such that approach is made at speed at which insertion is difficult, and evaluate effects of photosensitizing on injection efficiency Number of days passing after injection (days)

BAT-LY-Light: LY+BAT containing liquid; photosensitizing injection; attempted on 32 cells
BAT-LY: LY+BAT containing liquid; normal injection; attempted on 30 cells
LY: LY containing liquid; normal injection; attempted on 29 cells

SITE-SPECIFIC CELL PERFORATION TECHNIQUE

TECHNICAL FIELD

The present invention relates to a method for perforating a membrane by partially treating the membrane (cell membrane, etc.) with a membrane-denaturing agent, etc. It also relates to a membrane-disrupting material having a membrane-denaturing effect.

BACKGROUND ART

In gene therapy and artificial substance production systems using living organisms, means of introducing a nucleic acid, a protein, and such, into the interior of a cell are extremely important. On the other hand, techniques for extracting structures such as the nucleus of a cell, are also gaining wide attention. In other words, it can be said that injecting and extracting substances into/from cells, the basic unit constituting organisms, is a fundamental technique of bioengineering.

Conventional substance introduction techniques can be roughly categorized as follows:

a) Introduction techniques targeting non-specific cell groups b) Introduction techniques targeting a specific cell Examples of technique a) are, those using viral vectors (retroviral vectors, etc.), non-viral vectors (lipofectin, etc.), electroporation, calcium phosphate method, particle-gun method, etc. Technique b) could be exemplified by the microinjection method ("Fundamental techniques of gene therapy", Youdosha (1995)).

Generally, technique b) is used against large cells, such as egg cells. One reason for this is that the microinjection method uses shear force of a capillary glass tube to disrupt the cell membrane, and therefore, a technical limit probably arises due to the cell size. Also, this method requires skilled experience on the part of the handler, and therefore, automation is difficult. Furthermore, in many cases the pipette cannot be inserted due to the flexibility of the cell membrane of normal cells, except egg cells.

In technique a), a non-specific cell group is randomly treated, and it is hoped that the objective substance will be introduced to a part of the cell group. Therefore, very rarely does the objective substance get introduced into all cells. Also, it is generally difficult to separate only cells into which the objective substance has been introduced.

Moreover, a sophisticated micromanipulator is required to extract structures within the cell without causing them any damage, having drawbacks similar to the above microinjection method.

Thus, at a time when cell treatment has become a routine technique in medicine/engineering, the enhancement of reproducibility/precision of cell treatments is a vital issue. For example, when treating reproductive cells, considering that only an extremely small amount of egg cells can be obtained from each individual animal compared to somatic cells, an egg cell is a valuable genetic resource. Therefore, the fact that the success rate of their treatment largely depends on the technical experience of the technician is a grave problem from an engineering point-of-view.

Furthermore, all the above treatments were limited to single cells, migratory cells, or cells such as cancer cells that could be isolated/re-introduced from/into the body. Therefore, it was extremely difficult to modify treatments so that they could be used for cells that are inseparable from the body, such as nerve cells.

Other than the above examples, the possibility of technological developments that owe to cell modifications is on the increase. A few typical examples are, 1) To produce cloned animals, it is necessary to inject the nucleus as or chromosomal genes via the egg cell membrane, but the success rate of this procedure, is extremely low.

2) It a specific cell into which a magnetic structure has been incorporated can be made, it will be possible to magnetically control the location of the cell. The method of introducing magnetic bacteria-derived magnetosome-formation gene is generally used, and although there are successful examples, in most cases it is suitable to insert artificial magnetic structures when using cells, and such, for medical purposes.

3) When preparing micromachines such as micro surgical instruments, it is easily postulated that a cutting output sufficient for dissecting the cell membrane would not be obtained by mere physical means. Also, membrane disruption by mere chemical reactions would have problems regarding the regulation of the disruption.

4) In measuring action potential/electric stimulation of nerve cells, the measurement/stimulation were both done extracellularly by practical electrodes, except in fundamental research. This was the causative problem impeding the enhancement of precision, since it weakened the detection signal and increased stimulation input compared to the potential threshold value involved in original neuro activities. If it is possible to implant an electrode within nerve cells, not only would a measurement/stimulation equivalent to the original potential threshold value of nerves become possible, it will also enable information exchange between the electrode and nerve with a one-to-one precision.

5) In the field of energy conversion engineering, studies on placing micro photoelectric converting elements comprising photo potential onto artificial membranes are being conducted aiming at artificial photosynthesis. This approach aims to use the electromotive force given by photoelectric converting elements to generate transmembrane potential. If it becomes possible to place such micro photoelectric converting elements within cell membranes/mitochondrial membranes, it will enable the use of light to supply the energy needed for cellular metabolisms. Namely, it might be possible supplement various cells the ability to use photo energy just as the plants do.

DISCLOSURE OF THE INVENTION

A fundamental problem underlying these cell treatments is the lack of techniques that could control the disruption of the cell membrane. Various toxins have been examined for long for the purpose of just disrupting the cell. However, they could not respond to the demands of cytoengineering, which is to partially, and temporarily disrupt the cell membrane without causing cell death. Also there were limitations to the method utilizing physical shear force by using micro glass tubes, etc. The present invention attempts to resolve the issue of developing a technique by which a biomembrane could be perforated using a method other than physical shear force while regulating the disruption of the membrane, namely developing a membrane disruption regulating technique.

Though there are various membrane disruption techniques as mentioned above, those that could site-specifically disrupt a membrane were limited. Microinjectors and micromanipulators cause partial membrane disruption, however, they relied on physical shear force to disrupt and perforate the membrane. Namely, another issue that the present invention attempts to resolve is to develop a component for perforating a biomembrane while regulating the disruption using a method other than physical shear force.

What is needed for perforating a biomembrane while regulating the disruption of a biomembrane, is the regulation of the site and degree of disruption. Therefore, the inventors conducted zealous investigations on which methods would enable the denaturation and perforation of a membrane while regulating the membrane disruption activity.

Enzymatic disruption using lipases and proteases, and methods using β-rays and laser-beams could be exemplified as methods that partially and temporarily disrupt a membrane. However, the inventors focused their attention on the phospholipid radical sequential peroxidation reaction.

Active oxygen such as singlet oxygen, and superoxide radicals peroxidize unsaturated phospholipids of the cell membrane by sequential reactions. As countermeasures, cells have radical scavengers such as α-tocopherol (vitamin E), and L-ascorbic acid (a water soluble anti-oxidant; vitamin C), superoxide dismutase (SOD) and such oxidation defense mechanisms, to resist oxidation ("Free Radicals in Biology and Medicine", Oxford university Press (1985)).

When such sequential oxidations exceed the oxidation defense capacity, phospholipid membrane disruption rapid progresses in an exponential manner, and the cell becomes unable to maintain metabolism as the membrane loses its permeation inhibiting capacity. If these sequential reactions progress further, the cell will ultimately perish.

Photosensitizers (PS) are molecules that trigger such lipid sequential peroxidation reactions by producing active oxygen using light. Rose Bengal, porphyrin, and such can be given as photosensitizers in general use.

By utilizing such photosensitizers as membrane-denaturing agents, when denaturing the membrane, it will be sufficient to conduct sequential peroxidation reactions partially on the minimum objective cell surface, for a short period of time. Furthermore, the membrane damaged by the sequential peroxidation reactions at the time of membrane perforation, is expected to be repaired after the perforation by the fluidity of the membrane itself, or by the aforementioned anti-oxidation systems.

The inventors coated terthiophene (5'5"-bis(aminomethyl)-2, 2':5',2"-terthiophene dihydrochloride), a type of photosensitizer, on the surface membrane of the nerve cell line PC12. Photosensitizers are membrane-denaturing agents that could be controlled by light exposure. By measuring membrane resistance, the inventors revealed that membrane resistance, namely, the ion permeability of the membrane increases due to the action of the photosensitizer, which is activated by exposing the whole cell to laser beams. Furthermore, by controlling the amount of beams and amount of photosensitizer, the change in membrane resistance caused by laser beam exposure could be regulated in at least three ways:

1) No change in membrane resistance
2) The resistance decreases and then recovers
3) The resistance is lost Noteworthy is the fact that the inventors found that the duration it takes for the membrane permeability to recover to the state prior to disruption, was around 30 sec at suitable conditions.

Also, a similar change in membrane resistance was observed when only the axon of the cell was exposed to laser beams.

To examine whether membrane denaturation by photosensitizers could be applied for introducing substances into cells, the inventors attempted the adaptation into microinjection treatment. At the time of microinjection treatment, an injection solution containing Lucifer Yellow CH (LY), a water-soluble fluorescent dye, was prepared, and the ability to inject LY into PC12 cells was used as the determining indicator of the success of the injection. The injection was also automated by using an electric manipulator to exclude, as much as possible, man-induced influences on the evaluation of the success rate.

Using such an injection treatment system, the inventors evaluated how the success rate of the injection varied according to the presence or absence of the photosensitizer, terthiophene (5'5"-bis(aminomethyl)-2,2':5',2"-terthiophene dihydrochloride, 100 µM) within the injection solution, and according to the presence or absence of a two-minute exposure treatment by a 100 W mercury lamp was done, was measured.

As a result, when light exposure was done using a photosensitizer-containing injection solution, the success rate of the injection turned out to be 80%. Other controls resulted in an approximately 0 to 10% success rate. Therefore, by utilizing membrane denaturation, a significant improvement in the success rate of the injection was accomplished.

Furthermore, the inventors compared the cell survival rate between photosensitizer-treatment and normal treatments taking the LY retention rate of cells following injection treatment as the indicator of cell survival. 90% of the photosensitizer-treated cells survived for three to six days, whereas normally treated cells had a survival rate of only 10%, the survival rate of photosensitizer-treated cells being significantly high.

These results show that compared to injection techniques using physical shear force, those using membrane denaturation are clearly superior as means that suppress damage to cells.

The above results showed that suitable membrane perforation is possible by combining a photosensitizer and light. Namely, conditions in which the cell membrane is repaired without the cell being perished can be easily discovered. Naturally, it goes without saying that by preparing a membrane-destroying member by coating a membrane-disrupting material such as a photosensitizer on a support, the membrane could be contacted with this membrane-destroying member easily.

For example, this membrane-destroying member could be contacted with cells by utilizing a floating membrane-destroying member, for example microbeads coated with a membrane-denaturing agent, and contacting this membrane-destroying member using laser tweezers. Under such contact conditions, it is also possible to start the membrane denaturation reaction and then introduce this membrane-destroying member into cells. The membrane-denaturing agent itself may be a membrane structure, such as a micelle.

Furthermore, the inventors converted the scanning probe of the atomic force microscope into an electrode, and coated the probe-tip with the photosensitizer 5'5"-bis(aminomethyl)-2,2':5',2"-terthiophene dihydrochloride to create a novel component. When this photosensitizer-coated component is inserted into the cell membrane, resistance caused by the cell membrane could be observed between the electrode within and without the membrane. Since the physical shear force of the electrodes of the atomic force microscope is not intense enough to cause cell perforation, the newly prepared component showed that it could be used as a component that is equipped with both the electrode function of the atomic force microscope and the controllable membrane-disrupting function. Also, by coating or fixing photosensitizing compounds onto already existing numerous components, it is possible to give these components the controllable membrane-disrupting function in addition to their original functions.

Namely, the present invention features:

(1) a method of denaturing or perforating a specific site of a membrane. the method comprising contacting the whole or part of the membrane with a reagent containing a specific compound that induces a membrane-denaturing reaction by a specific stimulation, and giving said stimulation;

(2) the method of (1), wherein the membrane is a cell membrane, a cell wall, a biomembrane, or an artificial membrane;

(3) the method of (1) or (2), wherein the region stimulated is included in the region contacted with the reagent;

(4) the method of (1) or (2), wherein the region contacted with the reagent is included in the region stimulated;

(5) the method of (4), wherein the reagent is contacted using a support;

(6) a method of any one of (1) to (5), wherein the specific stimulation is light, and the compound is a photosensitizing compound;

(7) a membrane obtained by the method of any one of (1) to (6), wherein the specific site has been perforated or denatured, or a membrane structure containing said membrane;

(8) the membrane or membrane structure containing said membrane of (7), wherein the membrane is a cell membrane, a biomembrane, or an artificial membrane;

(9) the membrane structure of (7) or (8), which is a cell, a micelle, or a liposome;

(10) a method of injecting a compound into a structure, the method comprising mixing the structure of any one of (7) to (9) with a complex comprising a compound to be injected and a carrier;

(11) the method of (10), wherein the carrier is a liquid or solid;

(12) a method of (10) or (11), wherein the substance is a nucleic acid or protein;

(13) a membrane-destroying member for denaturing or perforating a specific site of a membrane, which comprises a support, and a membrane denaturation promoting portion comprising a membrane denaturation force other than physical shear force, which was formed on at least one site on the surface of the support;

(14) the membrane-destroying member of (13), wherein the support is rod-shaped, tube-shaped, needle-shaped, or spherical;

(15) the membrane-destroying member of (13) or (14), wherein the membrane denaturation promoting portion is coated or fixed with a compound that generates the membrane denaturation reaction at the membrane denaturation promoting portion;

(16) the membrane-destroying member of (15), which utilizes a sequential peroxidation reaction of the membrane components, in which the membrane denaturation reaction is started by a direct/indirect production reaction of reactive oxygen species;

(17) the membrane-destroying member of (15) or (16), wherein the membrane denaturation reaction is induced by a specific stimulation and reaction precursor, and includes the reaction which denatures or perforates the membrane;

(18) the membrane-destroying member of (17), wherein the specific stimulation is light, and the reaction precursor is a photosensitizing compound;

(19) the membrane-destroying member of any one of (13) to (18), wherein the support penetrates the membrane following membrane denaturation or disruption, and said penetrated membrane closely contacts with said support;

(20) the membrane-destroying member of any one of (13) to (19), wherein the membrane is a cell membrane, a biomembrane or an artificial membrane.

As to the combination of the compound and stimulation used for denaturing or perforating the membrane, any combination may be used, as long as it can perforate the membrane in a controllable manner, without completely destroying the membrane. As to the stimulations used, electromagnetic waves including light, particle rays including radiation, heat, cooling, electricity, magnetism, oscillations including ultrasonic waves, physical contact, chemical substances, as well as, living beings in general including cells, viruses, and such can be given as examples. These stimulations may be used alone or together with others.

As compounds that are used to denature and perforate the membrane, enzymes involved in membrane denaturation and disruption, antibody molecules, membrane bound proteins, glycoproteins, lipids, and such may be used. Photosensitizers such as porphyrin, rose bengal, methylene blue, acid red, alpha-terthienyl, etc., or their derivatives may also be used. Oxidants such as reactive oxygen species, reductants, explosive compounds such as nitro-glycerin/picric acid, magnetic particulates/magnetic fluids, metal particles/conductor particles/insulator particles/photoelectric converting elements/piezoelectric elements, and such may also be suitably used. These compounds may be used alone or together with others.

The membrane to be denatured or perforated, may be a membrane containing photoelectric converting elements and piezoelectric elements, or may be cell membrane or cell wall of animals/plants, biomembranes, or artificial membranes. As a biomembrane, a cellular coat including cell wall, cellular inner membrane including cell membrane, nucleus membrane, viral membrane, cytoplasmic micro tubule, microsome membrane, golgi apparatus membrane, lysosome membrane, endoplasmic reticulum membrane, tonoplast membrane, plastid membrane, peroxysome membrane, ribosome membrane, mitochondrial membrane, and such can be given. These may be combined to make a reconstituted membrane. Examples of artificial membranes are, protein membranes, lipid membranes, high molecular (collagen, etc.) membranes, metal membranes, conductor membranes, mitochondrial membranes, insulator membranes, electric conductive high molecular (such as polyacetylene, polythiophene) membranes, etc.

As membrane disruption methods the following are provided.

First is the method, wherein a compound is contacted with the cell membrane, and a part of the contact region is stimulated to denature or perforate only a range smaller than the region where the compound and the membrane contacted. For example, by exposing light through a micro slit against cells treated with a water-soluble photosensitizing compound solution, only the cell membrane portion that was exposed can be denatured, or perforated.

Second is the method, wherein a compound is contacted with a part of the cell membrane, and a region larger than the contact region that is stimulated to denature or perforate only the region where the compound and the membrane contacted. For example, by coating a part of a micro support obtained by processing silicon crystals, contacting the region coated with the photosensitizing compound with the cell surface under a microscope, and stimulating with light, will cause membrane disruption only to the region contacted with the support.

Examples of supports having membrane-destroying member as constitutive elements are, crystals, macro compounds such as $C_{60}$, micro pipettes, glass micro electrodes, patch electrodes, metal micro electrodes, wires, whisker, living organisms including cells, magnetic particulates/magnetic fluids, metal particles/conductor particles/insulator particles/photoelectric converting elements/piezoelectric elements, micro structures such as micromachines, as well as objects in which these are conjugated.

Light is well used as the specific stimulation, corresponding compounds being photosensitizing compounds. Dyes can be generally used as photosensitizing compounds. Among dyes, porphyrin, rose bengal, methylene blue, acid red, alpha-terthienyl, etch, or their derivatives are well used.

By suitably using the above methods, a membrane in which a portion is denatured or perforated can be provided. Also, as a membrane structure containing a membrane that has been denatured or perforated, a membrane which could be fixed on crystal oscillators and electrode basel plates, and in which the resonance frequency/fluidity/adsorption and such physical features could be modified, or a membrane in which the permeability/permeable site of a substance could be regulated by contacting with a gas/liquid, and such membranes can be given. Also, it may be a membrane in which the cell membrane or cell wall of animals/plants, biomembranes, or artificial membranes has been membrane denatured/perforated. As a biomembrane, a cellular coat including cell wall, cellular inner membrane including cell membrane, nucleus membrane, viral membrane, cytoplasmic micro tubule, microsome membrane, golgi apparatus membrane, lysosome membrane, endoplasmic reticulum membrane, tonoplast membrane, peroxysome membrane, plastid membrane, ribosome membrane, mitochondrial membrane, and such can be given. These may be combined to make a reconstituted membrane. Examples of artificial membranes are, membranes containing a magnetic structure at a high density, protein membranes, lipid membranes, high molecular (such as collagen) membranes, metal membranes, conductor membranes, insulator membranes, electric conductive high molecular (polyacetylene, polythiophene, etc.) membranes, etc. As structures containing membranes subjected to denaturation and perforation, cells and micelles having a specific number of holes can be given. As cells, animal cells, plant cells, microbial cells, reproductive cells, somatic cells, and such can be given.

Compounds that are to be injected can be substances that permeate the membrane easily by normal diffusion, or substances that are to be passed through the membrane artificially in large amounts, specifically, nucleic acids, proteins, lipids, membrane structures, etc.

Carriers are gases, liquids, or solids that can be used to dissolve, or suspend the substance to be injected, examples being buffers in which nucleic acids are dissolved, etc.

The form of membrane-destroying member may be any used according to the objective, as long as it can carry out controllable disruption of the membrane. The membrane-destroying member contains a support and a membrane denaturation-accelerating site, and this membrane denaturation-accelerating site may be on the support surface according to the purpose, or may be a part of the surface. It may be kenzan (needlepoint flower holder)-shaped, spherical, needle-shaped, rod-shaped, tube-shaped, or may be provided in a combined shape of these. Examples of tube-shaped supports are, specifically, pipettes, tubes, injection needles, etc. Spherical supports could be beads that could be handled by the laser tweezer technique.

When coating or fixing a compound that generates a membrane denaturation reaction in a support constituting the membrane-destroying member, the methods that could be used are, solvent evaporation drying, spattering, vacuum deposition, plasma polymerization, chemisorption, physisorption, radical polymerization, ion polymerization, etc. The support and the compound may indeed be indirectly bound via a mediator.

When the membrane denaturation reaction utilizes a sequential peroxidation reaction of the membrane components that is started by a direct/indirect production reaction of reactive oxygen species, it is possible to initiate the production reaction by suitably supplying light energy, electrical energy, chemical energy, etc. Specifically, light is electromagnetic waves from the deep ultra-violet region to the deep infrared region with a wavelength of about 180 nm. Light due to laser oscillations may also be used. The above-described photosensitizing compounds may be used in this case as well.

When membrane denaturation or disruption is generated using membrane-denaturing component, there are cases where close contact of the penetrated membrane and the membrane-denaturing component or a support constituting the membrane-denaturing component is suitable. Namely, in the case of a membrane-denaturing component that is tube-shaped and is connected to a pump, and to which manipulations such as microinjection and micromanipulation could be done, it is suitable that the penetrated membrane and the membrane-denaturing component or a support constituting the membrane-denaturing component are in close contact at the time of substance transport into/out of the cell.

Membrane-denaturing component controllable by location controlling apparatus are also well used in cell treatments, etc. Examples of location controlling apparatus are, scanning probe microscopes of atomic force microscopes and such, laser tweezers, micromanipulators, etc. Specifically, as a support constituting the membrane-denaturing component, atomic force microscope's scanning probe, or the proximal light scanning microscope's scanning probe, and such could be used.

The present invention can be utilized as a technology in various fields by suitable simple-and-clear applications carried out by one skilled in the art. One example is indicated below.

First, as the membrane manipulation, membrane disruption/denaturation and other manipulations could be carried out on an objective membrane by ligating or using together with the membrane-denaturing or disrupting agent, a manipulator comprising the function of manipulating an object having a membrane such as a cells/viruses, and a binder having the ability to bind/contact the target membrane. The manipulator, binder, and the membrane denaturing or disrupting agent may be used alone, or one of these could serve as the other two. In this case, the target membrane is a liposome/cell membrane/intracellular organelle membrane/viral membrane, and such, and the binder is a polyclonal antibody/monoclonal antibody/metal beads/plastic beads/virus/cell/living organism, etc. Utilized environment may be within the atmosphere, within a liquid, within the body, etc. Examples of cell/virus manipulations are, denaturation/disruption/growth acceleration or suppression/transformation/cell death induction/division or fusion acceleration/agglutination or dissociation acceleration/substance uptake or excretion acceleration, etc.

The invention may also be applied as substance introduction/excretion techniques due to the temporary perforation of the cell membrane. For example, in the creation of clone animals, and gene therapy, the introduction of genes into cells is an important manipulation.

The invention may also be applied for cell fusion. It could be done by using the membrane denaturation reaction of the present invention, which utilizes chemical substances such as polyethylene glycol, and viruses such as Sendai virus, for the cell fusion treatment.

Furthermore, it is possible to create a battery using the cell membrane potential caused by electrodes inserted into the cell. A major problem carried by micromachines and internal therapeutic instruments, is the securing of a power source for operation. By using membrane-disrupting material and electrodes, the potential that is within and without the cell membrane could be used as the power supply, and it will be possible to construct a system having suitable cells as batteries. The present invention could also be applied to create ultra microsurgery tools for cellular levels, such as cell scalpels. Though there are various dissecting instruments such as various types of scalpels, even if they are very small instruments, they cannot go beyond dissecting tissues. Dissecting instruments usable beyond the level of cells did not exist until now, but the membrane disruption technique of the present invention could be applied for dissecting cell membranes and intracellular membranes such as nucleus membrane.

The present invention could also be provided as a disruption technique that could be used site-specifically for micelles/liposomes containing medications for drug delivery systems (DDS) used in gene therapy. Namely, DDS research for using the system intensively around the target affected area, while suppressing side effects of the medications are being carried out, and by applying the present invention for disrupting microcapsules containing medications, an effective DDS could be accomplished.

The present invention could also be applied in manipulations of cellular organelles. Namely, the above-described micromanipulators and microinjectors could be used to easily manipulate cellular organelles such as lysosomes and the nucleus, to enable effective cell treatments. Specifically, egg cell manipulations and such (clone creation, etc.) in reproductive engineering could be given as an example.

The present invention could also be used for novel function expression and arrangement of functional molecules targeting flat/spherical membranes. In biomembranes, membrane proteins having various functions drift within the membrane while exerting their diverse functions, such as metabolism of chemical substances/transmission of electrons within the membrane surface and within and without the membrane, carrying out the functions alone or in suitable fissions-fusions. Such functional expressions by combinations of migratory functional units within the membrane surface and outside the membrane, are exactly what could be called micro chemical plants. Using such functional expressions of biomembranes—the scene of reaction—as a model, if biological functional molecules, and artificial objects such as piezoelectric elements, photoelectric converting elements, and memory elements would also become incorporatable as membrane devices by controlling the intake of various functional units into artificial membranes and biomembranes using the membrane disruption/denaturation technique, it will be possible to construct reaction systems with an extremely high degree of freedom.

Furthermore, cellular functions could be expanded by membrane manipulations and addition of devices. Namely, by using the membrane perforation technique of the present invention, novel functions could be given to already existing cells, by fusing a cell and an artificial functioning body. For example, a leukocyte could be magnetically guided to an affected area by creating a leukocyte in which a micro magnetosome particle deriving from magnetic bacteria has been inserted. This is a novel technique that could be called, not only a drug delivery system, but also a cell delivery system.

Also, by incorporating a photoelectric converting element into a membrane, it is possible to furnish cells with a function that is specific to plant cells, which is the ability to convert the energy of light into a chemical energy.

Furthermore, by applying a photoelectric converting element incorporated in the cell membrane for the input/output of nerve cell signals, it is possible to connect nerve cells directly with a photo information-processing computer.

Use of micromachines for therapeutic purposes is drawing great interest. Since such micromachines need to be small enough to enter even blood vessels, the energy source becomes restricted. Namely, energy supply via wires is difficult, and on the other hand, energy that could be mounted on the micromachine is highly trivial. Therefore, it is clear that an output provided by physical means by a built-in energy source would be overwhelmingly insufficient to cause influences such as cell disruption and cell denaturation when using micromachines. It could be said that membrane-disrupting agents and activation of these are indispensable in cell treatment. As an example, by using a photosensitizer that is activated by infrared light such as porphyrin as the membrane disruptor, the energy needed for membrane disruption could be supplied from outside the body by infrared lasers, etc.

By connecting an electrode to each nerve, the present invention could also be applied to create a nerve interface that exchanges information between nerves and electronic information instruments. Neural information is normally transmitted by the alterations in the cell membrane potential, namely, by action potential. To generate and measure this action potential, various analyses are being carried out regarding nerve-electronic instrument interfaces that input/output neural information, termed neural interfaces, however the distance between the electrodes and cells, and the degree of accumulation have become drawbacks. Although glass microelectrodes used for fundamental research purposes can be inserted into the cell membrane, or adsorped onto it to enable direct measurement/manipulation of cell membrane potential, high density accumulation was impossible since these electrodes are made by heat-processing glass tubes with diameters of only a few millimeters. On the other hand, metal microelectrodes that could be easily accumulated by semiconductor processing techniques, carry problems in cell membrane penetration ability, and stimulation/measurement have been done extracellularly, which is inefficient and also carries problems in site-specificity. By combining the membrane perforation technique of the present invention and metal electrode technique, it is possible to perforate the cell membrane, and set up micro metal electrodes within the cell. This will create an ideal neural interface where a cell and electrode could be connected one-to-one, or where several electrodes could be connected to a single cell.

The present invention could also be applied for the elucidation of cellular functions of the body such as for fundamental research of the brain. Namely, for brain function analysis, it is vital to analyze reciprocal information exchange between nerve cells. What is done at present is loading membrane potential sensitive dyes into nerves, and simultaneously measuring multi points of neural activity by optical measurement of the alteration of membrane potential as alterations in absorbance/fluorescence. However, in this case, it is impossible to optically carry out inputs into nerves, and to provide inputs/outputs to nerves, there is no alternative but to rely on electrical means, namely, electrodes. Analysis of the neural information processing mechanism by culturing nerve cells upon basal plate electrodes to form an artificial network, and research of applying nerve cells themselves as computing elements are also being carried out. Even in this case, signal inputting into nerves has become the stumbling block. Electrodes upon basal plates are extracellular electrodes, and in order to give nerve cells a stimulation to reach action potential generating threshold, the situation was such that an action potential could be finally generated as a total sum of stimulations received by each nerve following stimulation of nerve cell population upon the basel plate. The keys in assembling electrodes for exchanging information with each nerve are, downsizing electrodes into the cellular level, and means for connecting electrodes to each cell. This objective could be fulfilled by inserting intracellular electrodes obtained by combining micro metal electrodes downsized by semiconductor processing techniques, and the membrane perforation technique.

The present invention could also be utilized for functional electrical stimulation, and such, and for enhancing the accumulation/precision of stress-measuring therapeutic electrodes As a part of rehabilitation medicine, a method called functional electrical stimulation is being used, in which metal electrodes are inserted into nerve bundles and electrical stimulation is given to improve nerve/muscle functions. At present, the method has not gone beyond stopped at setting up electrodes in a few places within the nerve bundle, and is insufficient in the aspects of site specificity/precision of the nerve stimulation. By conjugating the membrane perforation technique and already existing electrode accumulation technique, one-to-one joining of a nerve and electrode will become possible, and thereby, stimulating only the nerve that needs functional improvement could be accomplished.

The present invention could also be applied as a technique for transmitting signals from nerves to various artificial organs. Organs embedded within the body are controlled, not by direct neural information of the body, but strictly by indirect control. One example is artificial urethral valve control. These valves that are made by shape-memory metals, open by heating and close at normal body temperature. This problem is, that the closing and opening is controlled by an external heating device switch and cannot be directly controlled by the will of the patient. If stabilization/enhancement of precision of neural information becomes possible by neural interfaces using membrane-penetrating electrodes, these valves could be controlled as if they were a part of the body of the user. It is true that artificial urethral valves are used only a few times throughout the day, and the handling, the opening/closing, is also easy, and therefore, not much inconveniences are caused by switch manipulations outside the body in daily life. However, to control artificial organs that carry out more complicated acts in place of visceral functions, it is indispensable to make the control signal source be from autonomous nerves.

The present invention could also be used for connecting/controlling prosthetic hand/legs equipped with sensory organs and joints that are controllable similarly to the human body. At present, there is a remarkable enhancement in performance of externally powered prosthetic hands/legs for functional assistance following dismembering. However, the controlling information source utilizes myoelectric power left in the wearer in most cases, and the power is overwhelmingly short compared to the information amount originally needed to control the limbs. Also, the transmitting of sensation through the prosthetic hand/legs to the wearer is limited to just physical contact information via the area connected to prosthetic limb. Therefore, even if the handling of the prosthetic hands/legs is learned by training, the reality is that the limbs are being used while enduring major inconveniences. One of the reasons impeding the enhancement of features of prosthetic limbs, is the fact that the information exchange pathways between the wearer and the prosthetic limb are poor. If stabile/highly precise measurement of each neural information becomes possible by neural interfaces using membrane penetrating electrodes, by joining the interface to the nerve that was connected to the wearer's amputated limb, this nerve can be used as the controlling information source, and sensory signal input terminal. Namely, it will be possible to control a prosthetic limb equipped with a movement performance/sensory organ similar to the body.

The present invention could also be utilized for controlling an artificial sensory organ (visual/auditory) and connecting it to the body. Artificial inner ears for repairing auditory functions already exist. This substitutes the functions of the ear drum-inner ear through a microphone and signal converting circuit, and several tens of electrodes are set up in the cochlear organs, auditory nerves are stimulated electrically, and the auditory information is sent to the brain. The biggest reason why this instrument established itself as a therapeutic instrument is in the cochlear organs, in which auditory nerves are aligned according to frequency bands. Being a special case, information can be easily sent to the nerves from the electrodes in this instrument, but it is impossible to apply this electrode technique of the artificial inner ear to other organs. One of the technical targets is an electrode system sufficient to connect to the optic nerve, which contains one million neural axons per a 1 cm diameter, as the optic nerve is indispensable in repairing functions of the sense of sight, which among sensory organs is the most important information source of the body. Although such a highly dense, accumulative nerve electrode does not exist at present, the neural interface using membrane-penetrating electrodes will enable a highly dense accumulation able to respond to the optical nerve. Already, optical products using the charge-coupled device (CCD) has enabled one million picture elements at a low price, and using such photo information inputting instruments as functional artificial eyes, it will be possible to provide the human body with a sense of sight via the neural interface.

The present invention may also be used to expand brain functions. Although the brain, is energy-saving, has advantages such as parallel processing, and such, as an information processing device compared to semiconductor micro processors, it also carries weaknesses such as, the imprecision of information retention, difficulty of learning, etc. In order to overcome these weaknesses while taking use of the advantages of the brain, it is also possible to use together the brain and already existing semiconductor devices via the neural interface.

MODE FOR CARRYING OUT THE INVENTION

The invention shall be described with reference to examples below, but it is not to be construed as being limited thereto.

EXAMPLE 1

Culturing Nerve Cell Line PC-12

Cells of the established nerve cell line PC 12 used as a model of the central nervous system, are ganglia-like cells of adrenal medulla origin. These PC 12 cells were cultured using a NeuroBasal Medium (GIBCO BRL) (pH 7.3) containing 10% heat-inactivated horse serum, 5% bovine fetal serum, 7.35 mg/l L-glutamic acid, and 2 mM L-glutamine, under 95% $CO_2$.

Passaging was done by detaching cells from the walls of the culture flask by spraying culture medium onto cells, collecting cells by centrifuging at 300 g, for 5 min, inoculating 1 to $3 \times 10^4$ cells/cm$^2$ per 1 ml into a culture flask (IWAKI Glass) with a bottom surface area of 25 cm$^2$, and changing the medium every two to three days.

When differentiating PC 12 cells into nerve-like cells, 2.5 S of the mouse nerve growth factor (NGF) was added to the medium to a final concentration of 50 ng/ml. The method of preparing the NGF (Murine, 2.5 S) dispersed solution for adding into the medium is as follows.

1) Phosphate buffered saline (PBS; composition being, $KH_2PO_4$ 2.10 g/l, NaCl 90.00 g/l, $NaHPO_4 \cdot 7H_2O$ 7.26 g/l, pH adjusted to 7.4 by adding 1N NaOH) was prepared.
2) 2 mg of Bovine Serum Albumin (BSA) was dispersed in 1000 µl of the above-described PBS (pH 7.4), and the dispersed solution was sterilized by filtering through a 0.22 µm pore-sized filter.
3) The total volume was made into 200 µl by adding 100 µl of this sterilized solution to 100 µl NGF solution (GIBCO BRL), 8 µl of this solution was divided into mini-tubes, and cryopreserved at −20° C.

PC 12 cells were differentiated by adding the divided NGF solutions so as to dilute the solution 1000 times.

PC12 adhered weakly onto the walls of the plastic bottle, and grew while forming small clusters. Collagen dishes (IWAKI Glass) were used to culture the neuralyzed cells.

For the electrophysiological experiment described below, cells differentiated into nerve-like cells 6 days before were used.

EXAMPLE 2

Synthesis of 5'5"-bis(aminomethyly)-2,2':5',2"-terthiophene

Figure 1:
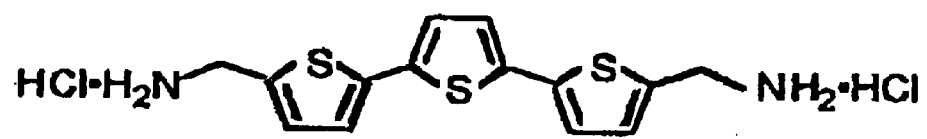
FIG. 1 shows the structural formula of the 5'5"-bis(aminomethyl)-2,2':5',2"-terthiophene (BAT) dihydrochloride.
Figure 2:
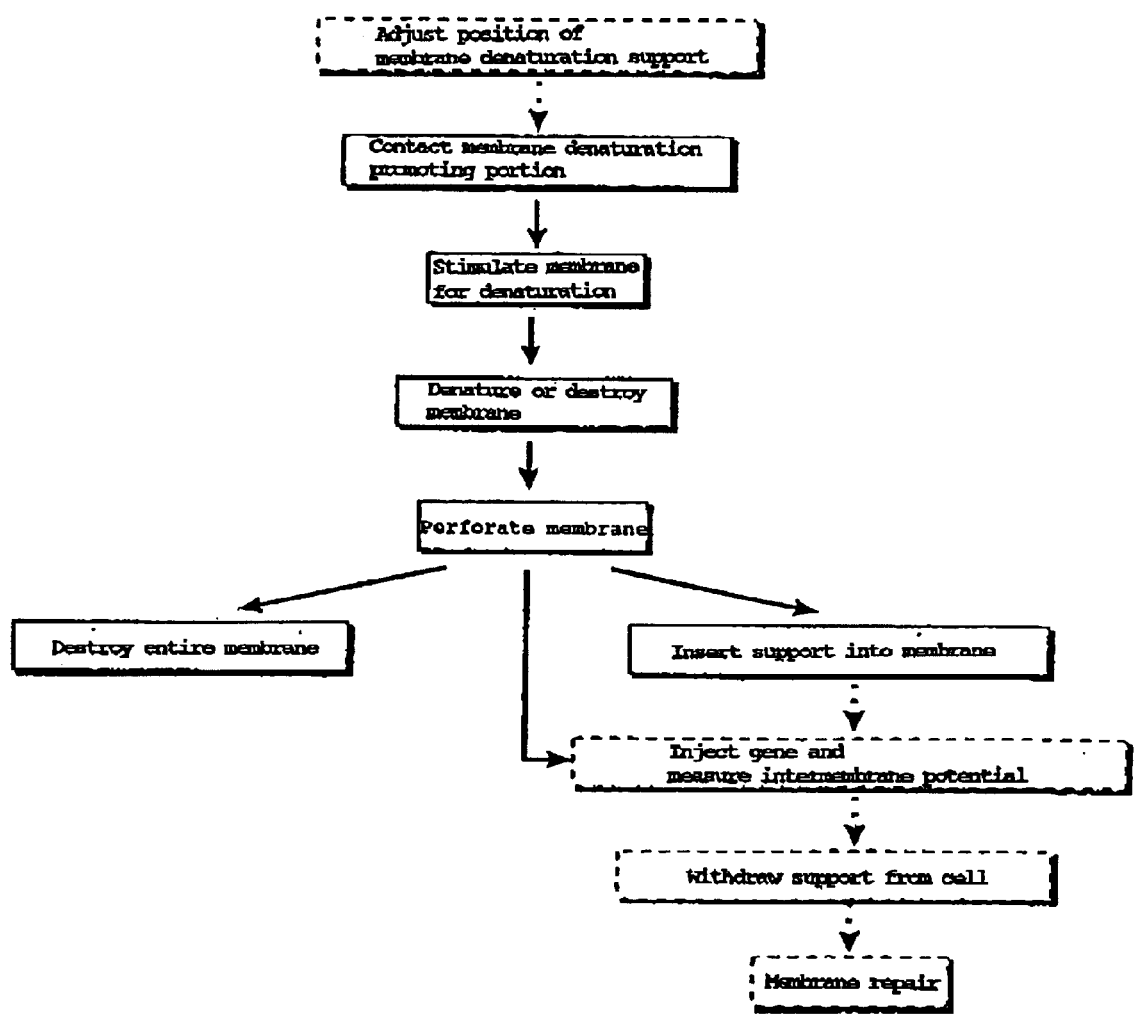
FIG. 2 shows the flow chart of membrane perforation technique.
Figure 3:
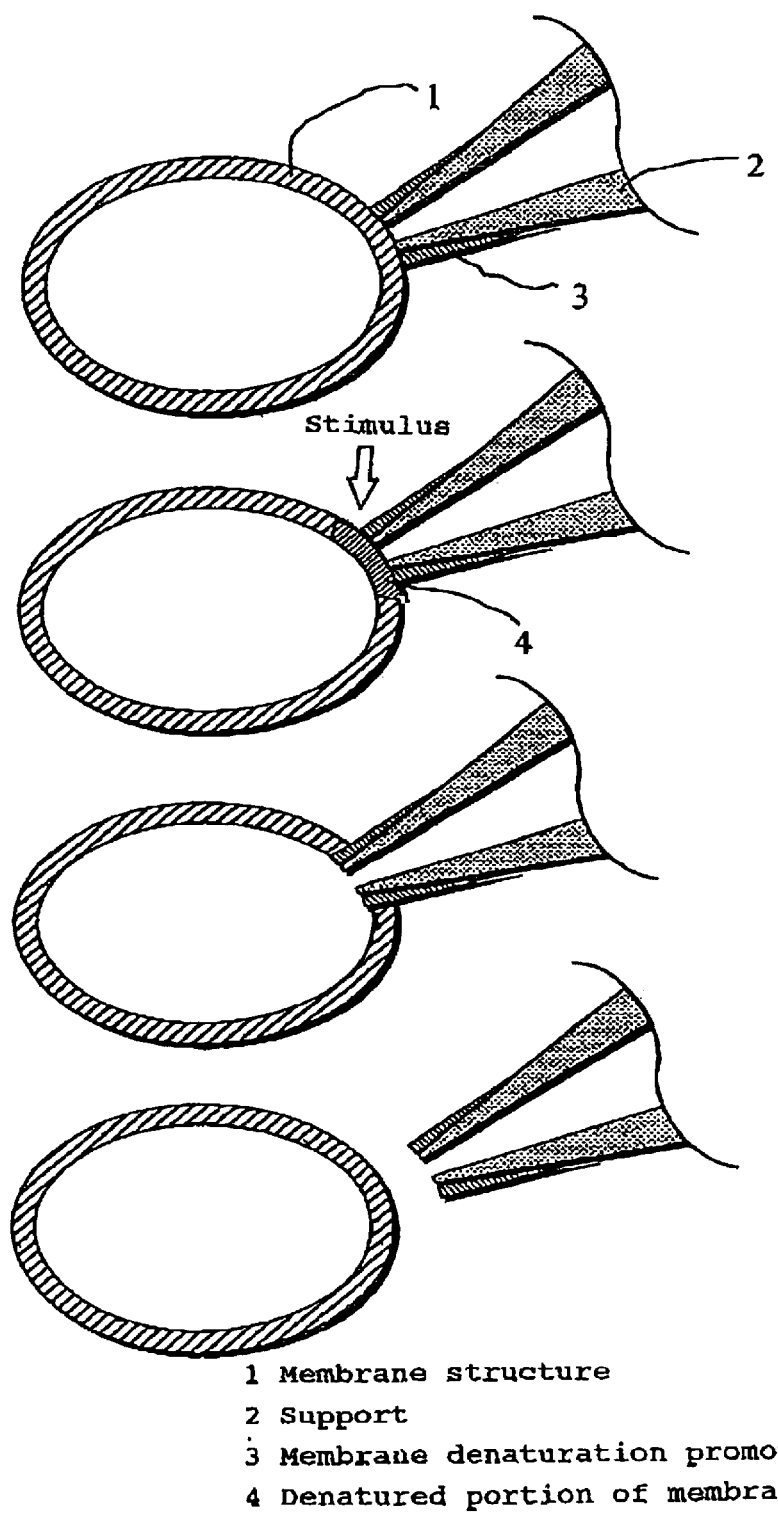
FIG. 3 shows an example of the relationship between a membrane-destroying member having a pipe-shaped support, and a membrane structure that is treated by the membrane-destroying member.
Figure 4:
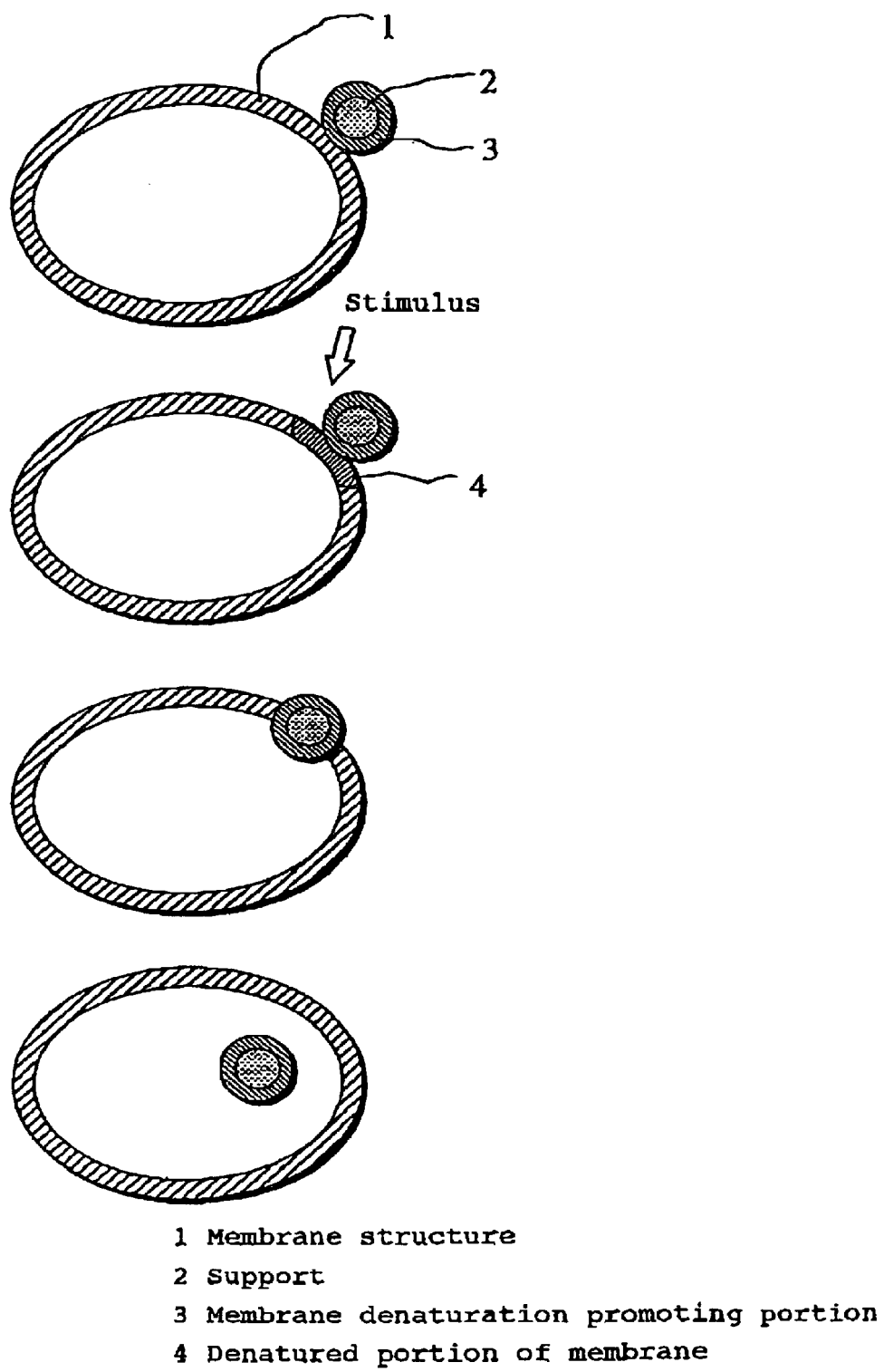
FIG. 4 shows an example of the relationship between a membrane-destroying member having a spherical or bead-shaped support and a membrane structure that is treated by the membrane-destroying member.
Figure 5:
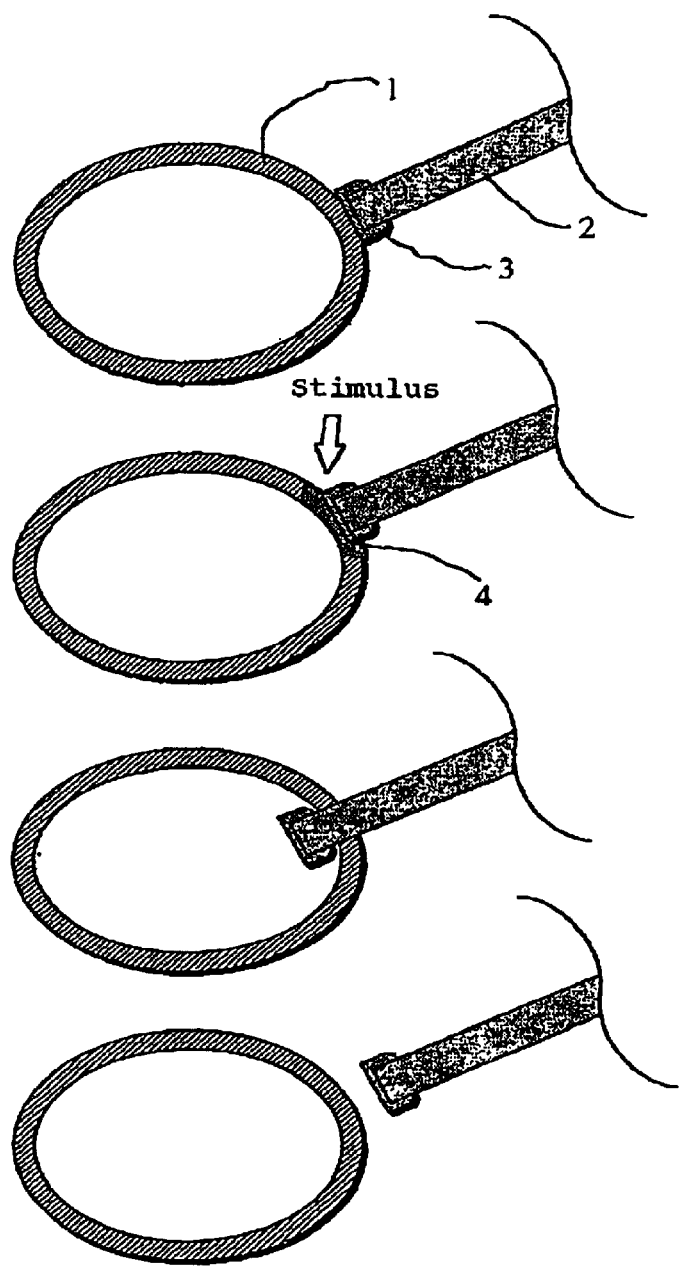
FIG. 5 shows an example of the relationship between a membrane-destroying member having a rod-shaped support, and a membrane structure that is treated by the membrane-destroying member.
Figure 6:
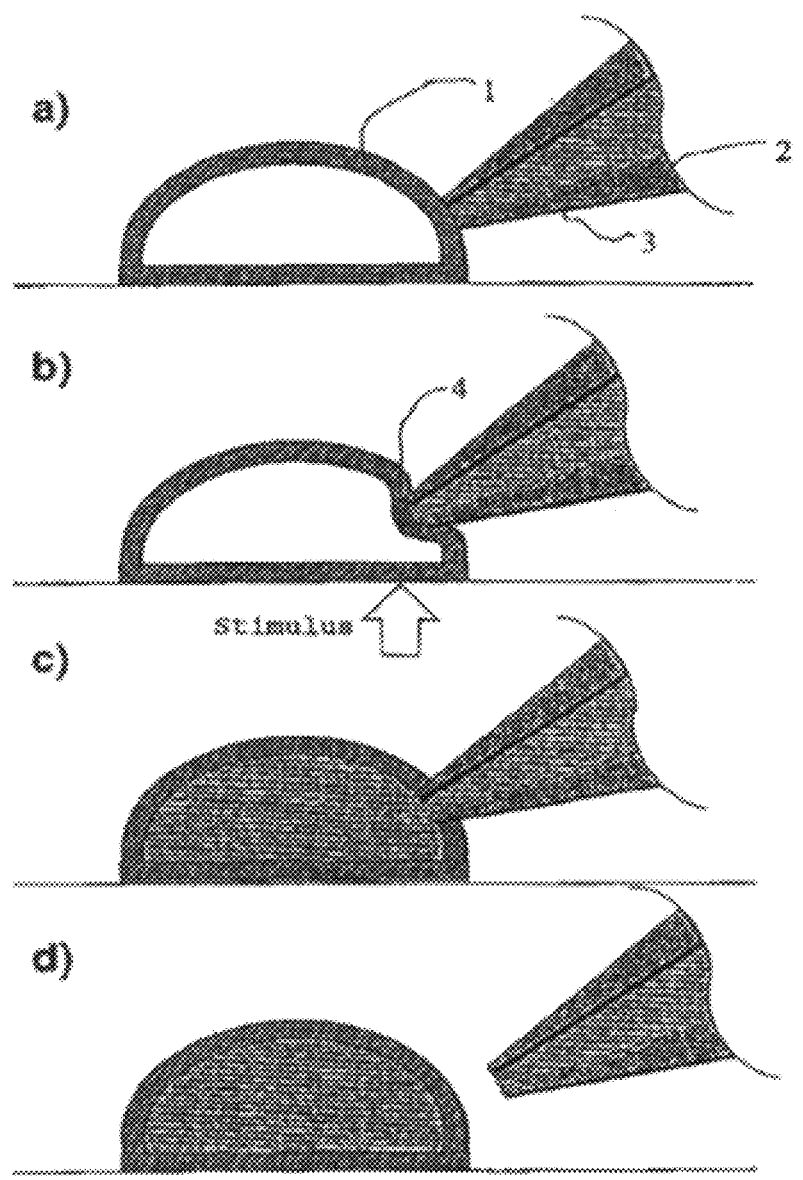
FIGS. 6a–6d show an example of the relationship between a pipe-shaped membrane-destroying member having a support maintaining a liquid containing a membrane denaturation promoter, and a membrane structure that is treated by the membrane-destroying member.
Figure 7:
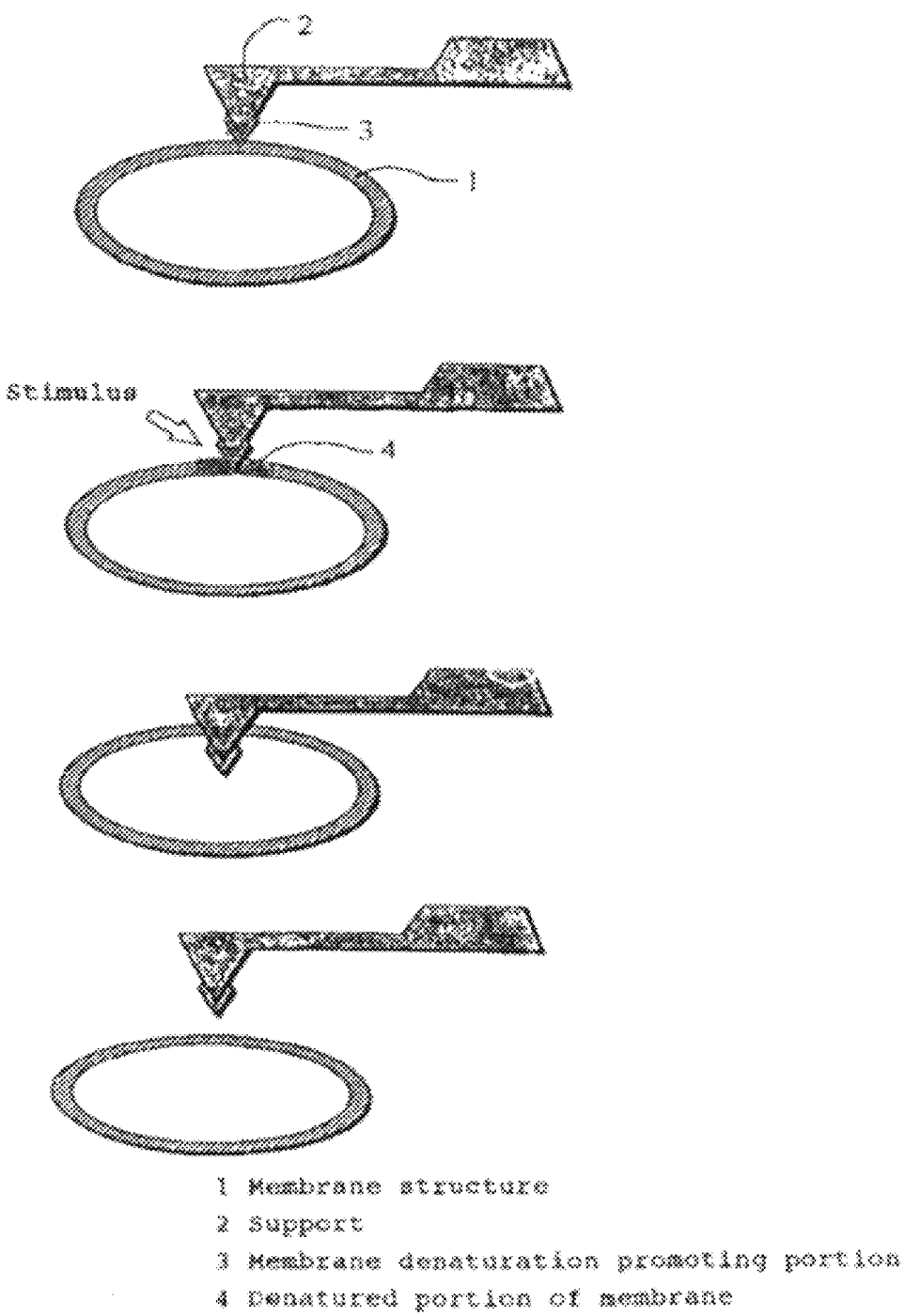
FIG. 7 shows an example of the relationship between a membrane-destroying member having an atomic force microscope probe-shaped support, and a membrane structure that is treated by the membrane-destroying member.
Figure 8:
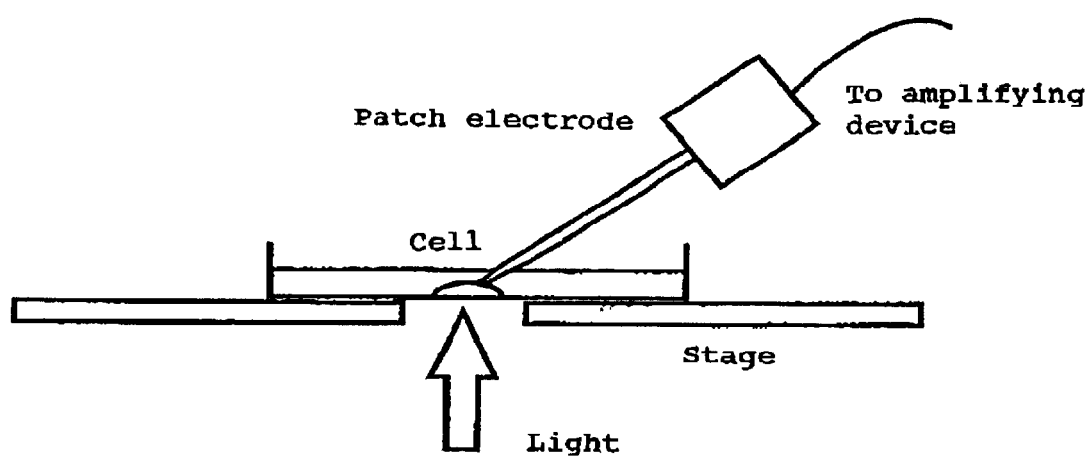
FIG. 8 is a schematic diagram showing an instrument for measuring intracellular potential and membrane resistance using a patch electrode.

The photosensitizer used was 5'5"-bis(aminomethyl)-2, 2':5',2"-terthiophene (BAT), a derivative of α-terthienyl. This compound was synthesized according to "Muguruma et al., J. Heterocyclic Chem., 33, 1–6 (1996)", and was provided in the state of BAT dihydrochloride. The structure of BAT dihydrochloride is shown in FIG. 1.

The thiophene oligomer having amino-methyl residue at the terminal, has a high solubility compared with other derivatives of the same type because of this amino-methyl residue. Solubility changes with the dissociation state of this amino-methyl residue. On the other hand, in the case of the BAT of the present invention, it has a bivalent positive charge within acidic aqueous solutions and dissolves easily. In aqueous solutions near a pH region suitable for the body (around 7.4), it has a feature of having both positively-charged monovalent BAT maintaining a high solubility, and non-charged BAT that agglutinates easily into a colloid state. Under this pH condition, by perfusing cells within a BAT-dispersed solution, this molecule can easily attach onto the cell surface. The hydrophilicity of BAT molecule is a novel feature that is not seen in either modified thiophene oligomers starting with α-terthienyl, or in other molecules designed as conductive high molecular monomers.

EXAMPLE 3

The Measurement of Membrane Resistance and Membrane Potential Following Light Exposure Since there is a need to monitor cellular level micro membrane damages, including the recovering process within seconds to a few minutes, the intermembrane potential of the cell membrane, or the ionic current passing through the cell membrane was measured using the patch clamp method, which is an electrophysiology experiment technique.

The photosensitizer BAT was dispersed in HEPES (25 mM, pH7.4) buffer. The BAT dispersed solution to be added topically near the cells by a micropipette had a BAT concentration of 2 mM, and the dispersed solution to be added throughout the perfusate had a BAT concentration of 0.2 mM.

Cells were incubated at room temperature within an electrophysiology experimental culture medium.

The culture medium used for this experiment had a composition of NaCl, 124 mM; KCl, 5 mM; $CaCl_2 \cdot 2H_2O$, 2.4 mM; $MgSO_4 \cdot 7H_2O$, 1.3 mM; glucose 10 mM, in which the pH was adjusted to 1.4 by finally adding NaOH. To prevent any influence due to evaporation, the electrophysiology experiment culture medium was changed every 40 min at the latest by a pipette.

BAT was added to a final concentration of 49 $\mu$M. Exposed light quantity was in three stages, being 0.47 $J/cm^2$, 0.94 $J/cm^2$, and 1.57 $J/cm^2$.

The solution within the patch electrodes had the composition of KCl 132 mM, NaCl, 8 mM, $MgCl_2$, 2 mM, HEPES 30 mM, $Na_2ATP$ 4 mM, GTP 0.3 mM, and EGTA 0.5 mM, in which the pH was adjusted to 7.3 by finally adding NaOH.

As the excitation power source, 50 mW, 363 nm argon ion laser standardly equipped within a confocal laser scanning microscope (CLSM) MRC-1000 UV (BIO-RAD laboratories) was used. $1/16^{th}$ ($1/4^{th}$ to the direction of the X axis and Y axis, 117 $\mu$m×170 $\mu$m) of the full screen of the microscope is scanned with the above-described laser beams. Adjustments were done so that the whole image of the patched target cell came into this area. 50 mW laser beam is a 100% output. According to the scanning speed, the exposed duration was selected from $1/16$, $1/4$, $1/32$ sec. The light reduction by the lens was also utilized. When the zoom function was used, the light is scanned on a concentrated area smaller than the normal area, and therefore, the light quantity per unit area increases in proportion to the square of the zoom magnification. Since the excitation light has to pass through the plastic of the collagen-coated dish before reaching the cells, there is a necessity to consider light reduction.

Also, in the excitation light exposure, a TTL signal coupled with an electrophysiological recording is suitably transmitted to the excitation light source, to synchronize the exposure and electrical measurement.

At the start of the electrophysiological experiment, the cell membrane potential was maintained between −80 to −60 mV. The resistance of the patch electrode was 3~4 M$\Omega$, and the above described solution was filled into electrodes, and used.

As for the amplifier for cell membrane potential measurement, Axopatch 1-D (Axon Instruments) was used. The membrane resistance was calculated by the change in membrane potential when a 1 Hz rectangular hyperpolarizing current was passed through for 350 mili sec. The amount of current passed through (0.1 or 0.15 nA) was selected so that the change in membrane potential due to the passing of current did not exceed 30 mV. Under these experiment conditions, PC12 cells did not generate action potential. The measured potential/current value was analyzed by Axoscope ver. 1.1 software (Axon Instruments). The result is shown in FIG. 9.

Figure 9:
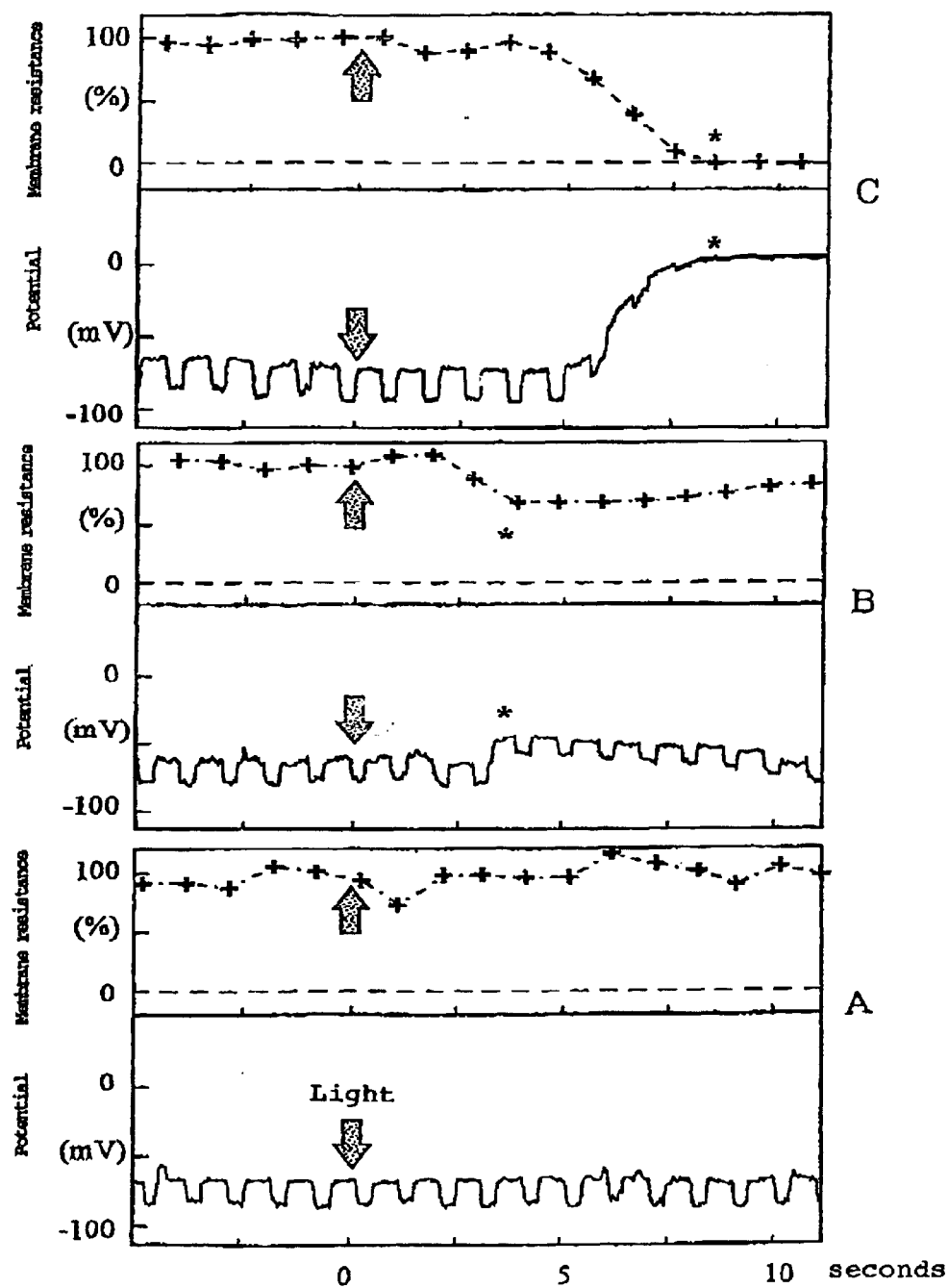
FIG. 9 indicates the relationship between the intensity of the light stimulation and alteration in cell membrane potential or alteration in membrane resistance.

In FIG. 9, the horizontal axis shows time lapse (unit;sec). In the vertical axis, the top box shows the cell membrane potential (unit; %) when normalization was done taking the value prior to exposure as 100%, and the bottom box shows cell membrane potential (unit; mV). Membrane resistance reflects membrane permeation inhibiting capacity, and membrane potential reflects the active ion transport capacity due to the functions of various intermembrane ion transportation systems and ion permeation inhibiting capacity.

For the light quantity of 1.57 $J/cm^2$, A was the weakest (0.47 $J/cm^2$), B was the second (0.94 $J/cm^2$), and C was the strongest (1.57 $J/cm^2$). In A, although cell membrane resistance/membrane potential changes a little following light exposure, a big change was not seen. In B, a decrease in cell membrane resistance/depolarization of the membrane potential occurred after a lag period of a few seconds. Also, under these conditions, it was seen that the resistance/potential recovered to the levels prior to light exposure after 30 sec. This is thought to be due to the membrane being repaired by vital reactions following a temporary disruption. In C, cell membrane resistance/membrane potential both disappeared in 8 sec after a few second lag period following light exposure, and was constant thereafter. This is thought to be due to a lack of a repairing reaction following a temporary disruption of the membrane, namely due to an irreparable membrane disruption.

EXAMPLE 4

The Treatment of Spraying RAT into Target Cells by a Micro Glass Pipette

A microinjector was connected to a micro glass pipette held by a micromanipulator, and BAT dispersed solution (BAT concentration was 2 mM, aqueous solvent) was filled into this micro glass pipette. The tip of this glass pipette was connected to a patch electrode and setup within 200 $\mu$m proximity of the cells in which the membrane potential/membrane resistance was to be measured. BAT dispersed solution was released by compressing the micro glass pipette to attach BAT onto the cell membrane of target cells. When laser beams were applied similar to Example 3, depolarization of the cell membrane potential was observed.

EXAMPLE 5

Microinjection Treatment Using Site-Specific Membrane Disruption

Introduction of substances using membrane disruption was applied for microinjection treatment.

To determine the success or failure of microinjection treatment, Lucifer Yellow CH(LY), a water-soluble fluorescent dye, was added to the injection solution. After injection treatment, if a yellow fluorescence of LY origin was observed within the cell by a fluorescent microscope, then, the injection treatment was judged to have been successful. The variation of the success rate of cell injection was evaluated by the presence or absence of the photosensitizer BAT within the injection solution, and the presence or absence of a BAT excitation light exposure.

Since LY is a low-toxic fluorescent dye used in microinjections, it has a feature of transmigrating into daughter cells at the time of cell division (Cell & Tissue Res., 234, 309–318 (1983)). Also, since LY is highly soluble in water, and is superior in diffusion, it is also used as a fluorescent labeling agent for nerve cells (Cell & Tissue Res., 254, 561–571 (1988)). It also has a feature of rapidly (in a matter of minutes) transmigrating between cells ligated by a gap junction, an intercellular liquid—liquid junction (SHIN-SEIRIGAKU TAIKEI 7 development/differentiation physiology, chapter 4, intercellular ligations I. Electrical bonds, IGAKU SHOIN, 1991). It was reportedly used as a similar gap junction formation marker in the PC12 cells utilized in the present invention (J. Neurosci., 14, 3945–3957 (1994)). Although LY-injected cells undergo cell death against an excessive LY excitation light exposure (Science, 206, 702–704 (1979)), the variation of the success rate of cell injection was evaluated by the presence or absence of BAT within the injection solution, and the presence or absence of a BAT excitation light exposure.

Normally, to make microinjection successful, a glass capillary having an opening with a diameter of a few hundred nanometers should be contacted with cells at high speed, to instantly penetrate/perforate the cell membrane or the nucleus membrane physically. For the experiments, a program operative electric micromanipulator (Eppendorf, Micromanipulator 5171) and electric injector (Eppendorf, Transjector 5246) were used, and it was possible to set the capillary contact speed to an arbitrary value. For the injection capillary, a mass-produced commercially available product made for the apparatus was used (Eppendorf, FemtoTips). Since the injection was automated by the electric manipulator, which resulted in a good reproducibility, and since a commercially available capillary with a highly conformed shape was used, compared to self-made capillaries, statistical processing of the success and efficiency of the injection could be easily done. The micromanipulator was attached to a fluorescence microscope (OLYMPUS OPTICAL, IX70 fluorescence microscope spec). Light of a 100 W argon lamp, which is the epi-illumination fluorescence light source equipped in the microscope, was treated by transmitting through an ultraviolet ray excitation filter set (OLYMPUS OPTICAL, U-MWU mirror unit), and the resulting ultraviolet light was used as the excitation source of the photosensitizer. The light exposing area was set to an approximately 100 $\mu$m diameter, according to the aperture of the fluorescence optical system of the microscope. Light of the 100 W argon lamp was treated by transmitting through an ultraviolet ray excitation filter set (OLYMPUS OPTICAL,U-MWU mirror unit), and the resulting ultraviolet light was used also as the LY excitation source for determining that LY has been injected into cells.

In such a system, the photosensitizer BAT is concentrated in the 0.5 $\mu$m diameter region in contact with the capillary, and as for the other areas, BAT was diluted rapidly by diffusion. Therefore, in the capillary contact region, when considering the BAT photosensitizing action produced by 100 $\mu$M BAT in the injection solution, BAT concentration at the areas other than the capillary contact region is thought to be negligible.

At the time of injection, after setting the operation range of the micromanipulator so as to allow the capillary to pierce cells at a contact speed 1000 $\mu$m s$^{-1}$, the capillary is operated at a low speed of 7 $\mu$m s$^{-1}$ and contacted with cells in such a manner that cell membrane is not perforated physically. Under these conditions, the change in the success rate of the cell injection by the photosensitizing action of BAT was compared.

The photosensitizer BAT used was that synthesized/provided by Muguruma et al. Commercially available products were used for the following reagents:

Sodium chloride (NaCl, Kishida Kagaku), potassium chloride (KCl, Kishida Kagaku) disodium hydrogenphosphate (Na$_2$HPO$_4$, Wako Pure Chemicals), potassium dihydrogenphosphate (KH$_2$PO$_4$, Wako Pure Chemicals), fluorescent marker Lucifer Yellow CH, Lithium salt (LY,ex.428 nm, em.536 nm. Molecular Probes).

The injection solution was prepared by dissolving the following compositions in purified water to the indicated final concentration (photosensitizer BAT 100 $\mu$M, HCl 50 $\mu$M, fluorescent marker LY 2 mM, NaCl 8 g/l, KCl 0.2 g/l, Na$_2$HPO$_4$ 1.15 g/l, KH$_2$PO$_4$ 0.2 g/l.

A control injection solution not containing BAT was also prepared.

As the target cells for the injection, established nerve cell line PC12 was used. This cell line was obtained from the Institute of Physical and Chemical Research (RIKEN) Cell Bank and was cultured according to Example 1. Cells to be injection treated were passaged to a $\phi$35 mm collagen coated dish (Iwaki Glass) at a cell density of 90000 cells/dish. The cells were incubated in a CO$_2$incubator (Forma Scientific), at 37° C., 5% CO$_2$, 95% air, and 100% humidity.

At the time of injection treatment, a Hib-A culture medium made by supplementing Hibernate A Media (Hib-A, Gibco BRL) [NeuroReport, 7, 1509–1512 (1996)] with 10% horse serum (Gibco BRL), 5% bovine fetal serum (Mitsubishi Chemicals, Dialyzed Fetal Calf Serum obtained from Nakashibetsu Calf), 7.35 mg/l L-glutamic acid (Gibco BRL), and 2 mM L-glutamine,) was used. The horse serum used had been heat-inactivated at 56° C. for 30 min.

For the above solution preparation, water purified by the water purification apparatus Biocel A10/Elix 10 (MILLIPORE) was used.

Figure 10:
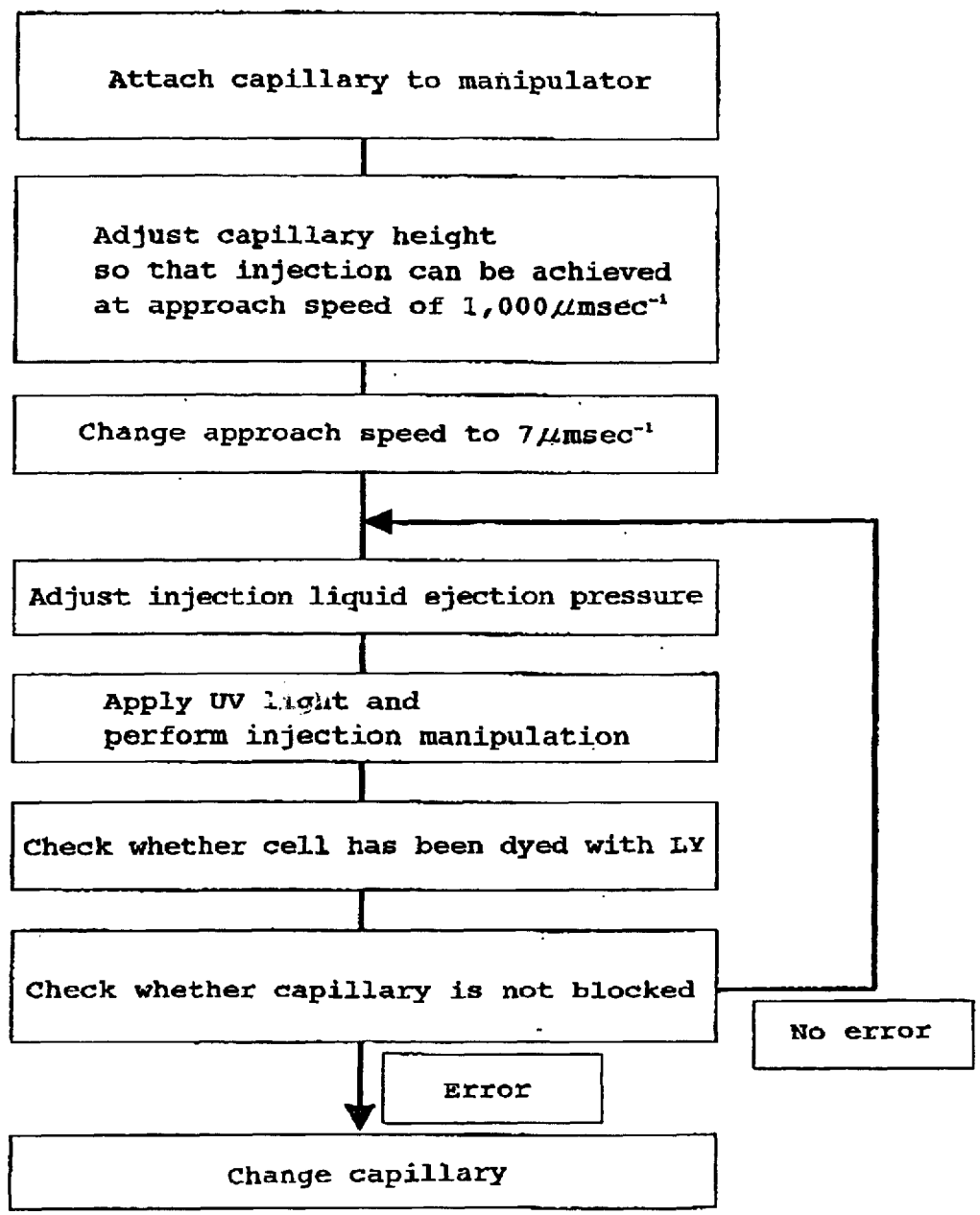
FIG. 10 shows the flow chart of an example of the photosensitizing injection.
Figure 11:
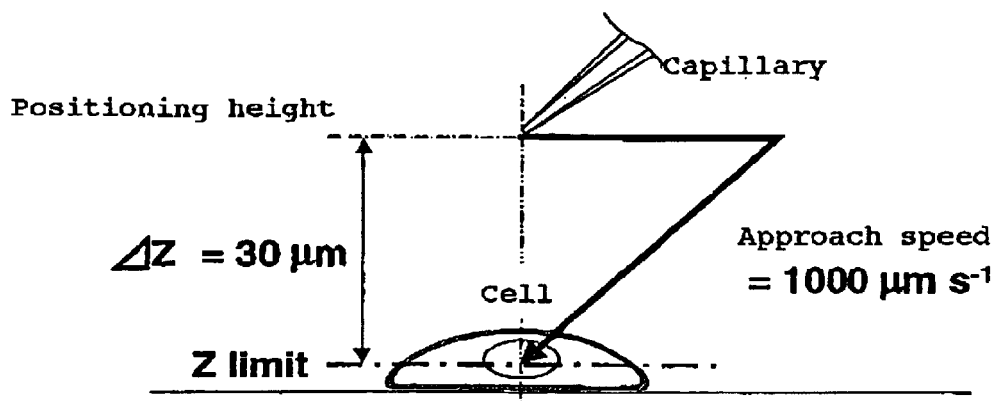
FIG. 11 shows a schematic diagram of an example of the photosensitizing injection.
Figure 11:
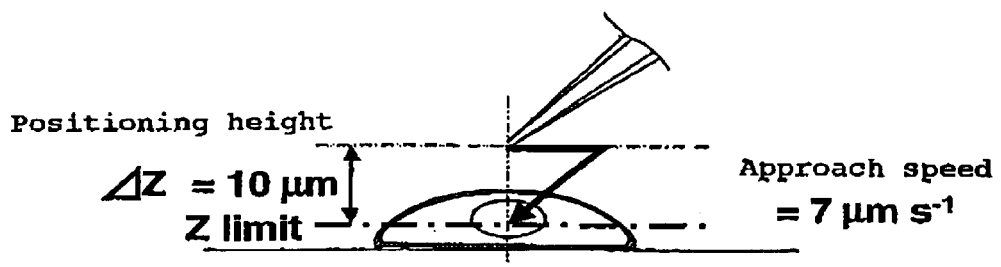

FIG. 10 shows the flow chart of injection treatment steps. Below is the relevant supplementary information.

1) At the time of injection treatment, all 3 ml of the NeuroBasal medium was removed from dish in which the cells were cultured, and the cells on the dish were washed by running 1 ml of phosphate buffered saline (PBS, 7.4, containing neither Ca nor Mg) (GIBCO BRL) over them. Then, all the PBS was removed, washed again with 1 ml of fresh PBS, then, all of this PBS was removed, and finally, the dish was filled with 2 ml of Hib-A culture medium for injection treatment. The cells were maintained in this Hib-A culture medium.

2) As for the micromanipulator used, in order to enable the capillary tip to pierce cells at the time of injection treatment, it was necessary to set the threshold position (Z limit) where the capillary tip nears moot to the face of the dish. The manipulator was set so that this Z limit position coincided with the position of the nucleus of cells on the dish.

3) The capillary position was altered to 30 $\mu$m above Z limit. The approach speed input value was altered to 700 $\mu$m s$^{-1}$ (effective value 1000 $\mu$m s$^{-1}$), and injection duration to 1.1 s (effective value 1.0 s) for other conditions as well. Under these conditions, the Z limit position was adjusted to enable a physical microinjection treatment with an 80% or more success rate against 10 or more cells. When the success rate fell, the Z limit was re-set.

4) The capillary position was altered to 10 $\mu$m above Z limit. The approach speed input value was set to 5 $\mu$m s$^{-1}$ and injection duration was changed to 124 s (effective value 120 s).

5) The epi-illumination fluorescence light source of the microscope was switched to violet excitation (U-MWBV mirror-unit) filter set suitable for observing LY fluorescence, and the release of LY from the capillary was observed by the Clear function (injection solution within the capillary is compressed with a pressure of 7000 hPa to remove clogging in the capillary). If the capillary is clogged, a new one was used.

6) The injection pressure was set to a pressure sufficient enough for a slow-release of LY from the capillary tip. The pressure sufficient enough for a slow-release of LY from the capillary tip had a wide range of variation from 10 hPa to 1000 hPa depending on the condition of the capillary tip, and therefore, suitable pressure corrections were done. The reason for this variation was the adherence of micro debris such as cell membrane fragments onto the capillary tip. When such debris adhered onto the capillary tip, the amount of the effective injection solution released varied significantly even when an equal pressure was applied, and hence, corrections had to be done.

7) in the visual field of the microscope, the cell position and capillary position were adjusted so that the capillary tip came onto the center of the cell. BAT was excited by applying ultraviolet rays, by switching the epi-illumination fluorescence light source to ultraviolet excitation (U-MWBV mirror-unit) filter set. To suppress the influence by light other than ultraviolet rays for excitation, the permeation light source for cell observation was shut-off.

8) Injection treatment switch of the manipulator was turned on. Capillary neared the cells, and after releasing the injection solution at that location for the set-duration, at the set-pressure, the capillary moved back to its original position. This whole process was carried out automatically.

9) After completing the injection treatment, the filter of the epi-illumination fluorescence light source of the microscope was changed from that for ultra violet rays to that for violet rays (U-MWBV mirror unit), LY excitation light was applied, and it was verified that cells had been LY-stained. When injection is done to dead cells, LY rapidly leaks out of the cell membrane and loses its fluorescence, and therefore, such cells are excluded from the data.

10) The permeation light source for cell observation is opened again, and while observing the cells, the capillary tip is positioned on the next cell.

11) Injection treatment is repeated from 5).

After injection treatment, Hib-A culture medium for injection treatment is removed from the dish, the dish is washed twice with 1 ml of PBS, and the culture medium is changed to 3 ml of NeuroBasal culture medium. Thereafter, the culture medium is changed according to normal procedure.

Penicillin/streptomycin mixture was added to the NeuroBasal culture medium used after the injection treatment to prevent contamination by fungi and bacteria.

When evaluating the success rate of microinjection due to the photosensitizing mechanism, it was necessary to carry out the injection under conditions in which the physical shear force of the pipette tip is not involved. To carry out a suitable injection, it is important to adjust the threshold limit to which the capillary can reach (Z limit). Therefore, the approach speed was lowered to 7 $\mu$m s$^{-1}$ after verifying that an injection with a success rate of 80% or more was possible at the set Z limit, under the normal approach speed of 1000 $\mu$m s$^{-1}$. At this approach speed, although the capillary reaches the same location as that when the injection succeeded, it hardly penetrates the cell membrane. Under such approach conditions where membrane perforation by physical force is difficult, the success rate of injection using the photosensitizing mechanism was compared. The results are shown in FIG. 12.

Figure 12:
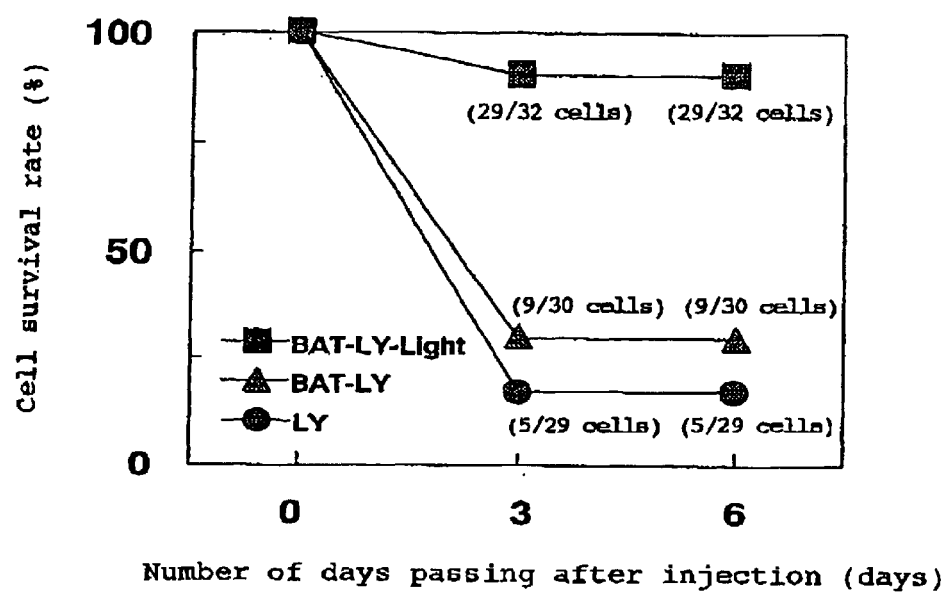
FIG. 12 shows a comparison of the success rate of the injection by a normal physical injection treatment, and the novel photosensitizing injection treatment.

In FIG. 12, the horizontal axis indicates the injection treatment conditions, and the vertical axis shows the success rate of the injection (unit; %).

When an injection solution using BAT was used, the inventors succeeded in obtaining an 80% success rate after a 2 min exposure of ultraviolet rays (succeeded in 25 of the 30 cells, 83%).

If the exposure was not done when the capillary was in contact with the cell, there was hardly any diffusion of LY into the cell (n=30, succeeded in 4 cells, 13%). Also, when an injection solution not containing BAT was used, the injection rate dropped to 0 to 10% (capillary approach speed 7 $\mu$m s$^{-1}$) irrespective of the presence or absence of an UV exposure (under UV exposure, succeeded in 0 out of 30 cells, 0%) (under no UV exposure, succeeded in 3 out of 30 cells, 10%)

The survival rate of cells to which microinjection treatment by a physical shear force was given, and that for photosensitizing microinjection treated cells were compared.

LY was injected into cells by microinjection. In dead cells in which the cell membrane had collapsed, LY rapidly diffuses, and staining is lost (Cell, 14, 741–759 (1978)). Therefore, LY maintaining rate of injection treated cells was used as an indicator of cell survival rate, and the survival rate after 3 to 6 days following injection treatment was compared. The results are shown in FIG. 13.

Figure 13:
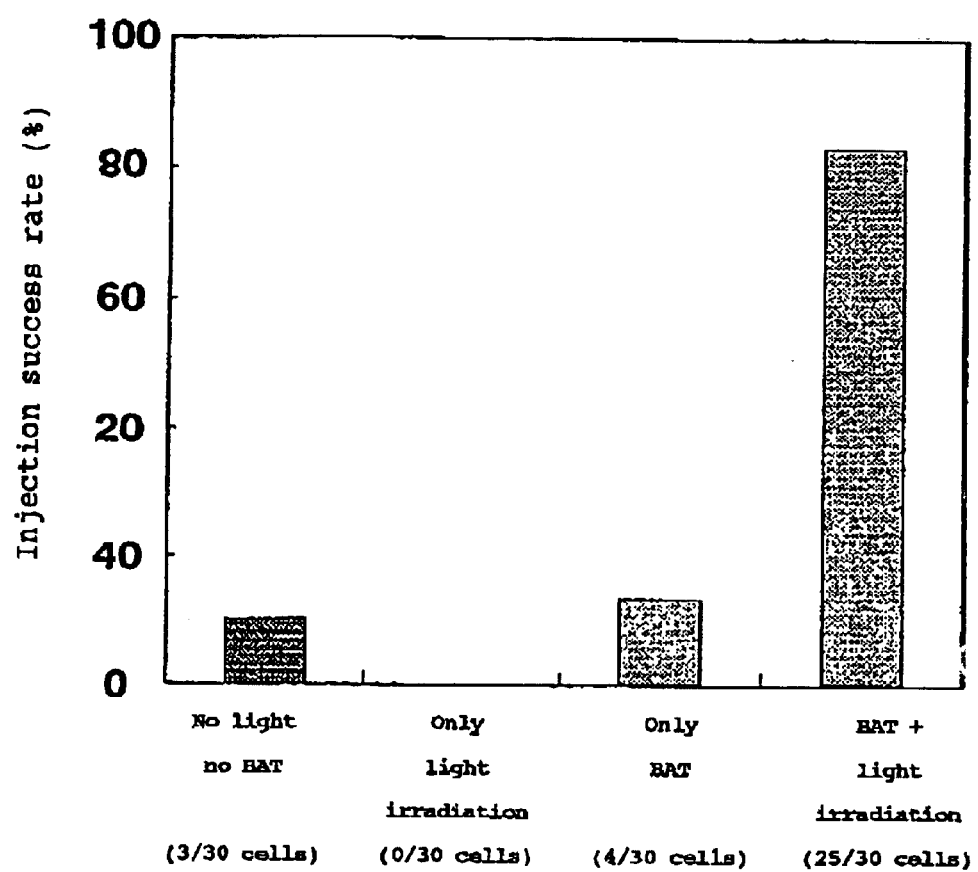
FIG. 13 shows a comparison of the alteration in cell survival rate by normal physical injection treatment, and the novelphotosensitizing injection treatment.

In FIG. 13, the horizontal axis indicates the number of days following injection treatment (unit, day), and the vertical axis shows the survival rate (unit; %).

Compared with the control where normal LY injection was done, the survival rate on the 3$^{rd}$ day following LY-BAT treatment was 30% or lower (LY:17%, BAT+LY:30%). On the other hand, in the photosensitizing injection-treated group, 90% of cells survived even after three to six days following injection treatment (BAT+LY+UV:91%). For all these three injection conditions, LY retention rate did not change during the 3$^{rd}$ to 6$^{th}$ days.

In the present injection treatment, when injection solution not-containing BAT was used, and when light exposure was not done, only a 10% of the cells were LY stained. Compared to such control treatments, when injection solution containing BAT was used, and light exposure was done, the success rate of LY staining was significantly high being approximately 80%. This shows that BAT contributed to cell perforation following light exposure.

After injection treatment, if it was a normal membrane shearing injection, the cell survival rate was 20 to 30%. Since cells treated by a photosensitizing injection had a survival rate of approximately 90%, it shows how little the cells are damaged by the photosensitizing injection.

LY injected into cells rapidly disperses into the cytoplasm and stains cells. However, in dead cells, in which the ion barrier ability of the cell membrane is lost, LY diffuse into the exterior of the cells in one to two seconds following injection. This rapid dispersion of LY has been reported to occur also through the gap junction, an intercellular liquid—liquid connection pathway (Cell & Tissue Res., 234, 309–318 (1983)) (J. Neurosci., 14, 3945–3957 (1994)). When considering these reports of rapid LY dispersion, in cells retaining LY after injection treatment, it is thought that perforated cell membrane has closed following injection treatment. Such a rapid membrane repair is also supported by the recovery of membrane potential/membrane resistance within a few minutes following light exposure, as shown in Example 3.

Two types of mechanisms are thought to be involved in this closing mechanism. One is due to the anti-oxidation mechanism of cells, by a metabolical repair of the oxidized membrane (J. Neurochem., 68, 1904–1910 (1997)). The other is not a physiological repair but the closing mechanism of the damaged site by the fluidity of membrane lipids (Proc.

Natl. Acad. Sci., 69, 2056–2060 (1972)) (J.Am.Chem.Soc., 94, 4475–4481 (1972)).

In the present injection treatment system, when the capillary is parted from the cell, the perforated site of the membrane is thought to close due to the flowing of cell membrane components that are unaffected by the photosensitizer. The fact that a similar cell membrane closing occurs even after a mere physical cell membrane perforation, can be given as a reason for the above assumption. Earlier, a physical cell membrane perforation by micro glass pipette and patch pipette was described. After such a physical perforation, in most cases, the perforated part of the cell membrane closes after the pipette is removed, and such a rapid re-closure is thought to be due to the fluidity/self-organizability of membrane lipids (Biomembranes and Bioenergy, Third edition, 7. The reconstitution of the biomembrane, Tokyo Daigaku Shuppan (1985)).

Membrane recovery due to biochemical metabolisms cannot result in membrane closing in a matter of seconds. Indeed, biochemical membrane repair may occur, however, such mechanisms may take a few hours to a few days to normalize an oxidized cell membrane.

When considering electrode connection techniques, the fact that LY had been injected into cells by a photosensitizing injection, is extremely significant. As mentioned earlier, LY is able to penetrate and stain not only cells into which LY is directly injected, but also adjoining cells connected via gap junctions (Cell & Tissue Res., 234, 309–318 (1983))[J. Neurosci., 14, 3945–3957 (1994)].

Intercellular electrical connection is one of the functions of the gap junction (SHIN-SEIRIGAKU TAIKEI 7 development/differentiation physiology, chapter 4, intercellular ligations I. Electrical bonds, IGAKU SHOIN, 1991). In such cells like cardiomuscular cells, a large number of muscle cells are electrically connected via gap junctions, and generate a synchronized contraction of the whole muscular tissue against an electrical stimulation.

Since cell-staining by LY was possible by the present BAT photosensitizing mechanism injection, it is thought that an electrical connection, at least to the extent of a gap junction, has been attained between the solution within the capillary and cytoplasm. Namely, this result suggests that an electrical connection was accomplished not by a physical perforation, but by light exposure.

By adding the photosensitizer BAT to the injection solution, and to carrying out injection treatment, the possibility of a light-regulated perforation technique that does not rely on physical shear force was shown. Furthermore, this technique was superior to normal microinjections that rely on physical shear force as it suppresses cell damage given by such injections.

EXAMPLE 6

The Creation of a Membrane-Destroying Member Using the Atomic Force Microscope Scanning Probe The probe-tip (the surface used for detection) of the commercially available, silicon single crystal scanning probe processed by etching (Nanosensors, silicon beam silicon single crystal scanning probe, cantilever 130 $\mu$m) was plated with a 220 mn layer of gold (Au) by spattering (Shibaura Seisakujo, spattering pressure 0.3 Pa, output 100 W). The areas other than the metal terminal at the detecting side, and the metal terminal at the instrument connecting side were insulated with a 100 nm layer of silicon dioxide. This scanning probe was equipped to the atomic force microscope (Nanoscope III, Digital Instruments), and the metal terminal at the instrument connecting side was connected to the minus electrode of an electroporation apparatus (Gene Pulser, BIO-RAD laboratories). The plus electrode of the electroporation apparatus was connected to the metal basel plate (copper, platinum, etc.) on the AFM sample plate, and prior to breakdown, namely, the probe-tip insulated by silicon dioxide, was connected to the basel plate. Also, a 3 M$\Omega$ resistance was serially connected between the scanning probe basel plate and electroporation apparatus, to prevent destruction of the scanning probe due to the excessive current that result after the breakdown of the probe. The electric capacity of the electroporation apparatus was set to 0.25 $\mu$F, the voltage to 50 V, and current was momentarily passed between the basel plate and probe-tip of the scanning probe. By this electrification, the insulation at the tip of the probe was destructed to expose the metal at the tip of the probe. Thus, a micro metal electrode was completed, in which only the probe-tip of the scanning probe was exposed.

This probe-tip of the micro metal electrode was immersed in a BAT 2 mM acidic solution (pH 3.0). By this manipulation, BAT was adhered onto the electrode. Finally, the electrode was washed with purified water to remove excessive BAT.

By the above process, a membrane-destroying member having both the function of a scanning probe of an atomic force microscope, and the function of an electrode was created.

These results showed the possibility of controlling perforation by light exposure by pinpoint use of photosensitizers in the connecting/embedding of various devices in small cells.

Industrial Applicability

A technique controlling membrane denaturation reaction other than physical shear force was developed. Thereby, it was possible to conduct membrane denaturation and membrane perforation more easily than by conventional techniques. For example, easy membrane penetration became possible where it was conventionally difficult with micro components constituting microelectrodes, micromanipulators, microinjectors, etc. Effective introduction of genes and such into cells also became possible.

What is claimed is:

1. A method of site specific regulated membrane disruption comprising:

contacting a membrane with a membrane-disrupting reagent that induces a membrane-denaturing reaction when the membrane is exposed to a stimulus, wherein the membrane-disrupting reagent is attached to a support which facilitates precise contact of the membrane-disrupting reagent with the membrane, wherein the membrane is separate and distinct from the support; and applying the stimulus to the membrane at a contact site under conditions effective to temporarily and partially disrupt the membrane only at the contact site where permeability of the membrane recovers to the state prior to disruption, wherein the stimulus is light, and the membrane-disrupting reagent is a photosensitizing compound.

2. A method of site specific regulated membrane disruption comprising:

contacting a membrane with a membrane-disrupting reagent that induces a membrane-denaturing reaction when the membrane is exposed to a stimulus, wherein the membrane-disrupting reagent is attached to a support which facilitates precise contact of the membrane-disrupting reagent with the membrane, wherein the membrane is separate and distinct from the support; and applying the stimulus to the membrane at a contact site under conditions effective to temporarily and partially disrupt the membrane only at the contact site where permeability of the membrane recovers to the state prior to disruption, wherein the membrane-disrupting reagent is a reactive oxygen species and the stimulus is selected from the group consisting of light energy, electrical energy, and chemical energy.

* * * * *